United States Patent [19]

Hirai et al.

[11] Patent Number: 5,344,953
[45] Date of Patent: Sep. 6, 1994

[54] FLUOROBENZENE DERIVATIVES

[75] Inventors: Kenji Hirai; Tomoyuki Yano; Mitsuo Yamashita; Emiko Ejiri; Tomoko Tateno; Kiyomi Aizawa, all of Kanagawa, Japan

[73] Assignees: Sagami Chemical Research Center; Kaken Pharmaceutical Co., Ltd., Tokyo, Japan

[21] Appl. No.: 145,209

[22] Filed: Nov. 3, 1993

Related U.S. Application Data

[62] Division of Ser. No. 823,454, Jan. 21, 1992, Pat. No. 5,281,742.

[30] Foreign Application Priority Data

Jan. 22, 1991 [JP] Japan .................................. 3-44589
Jan. 22, 1991 [JP] Japan .................................. 3-44590

[51] Int. Cl.$^5$ .............................................. C07C 69/96
[52] U.S. Cl. .................................................... 558/272
[58] Field of Search ......................................... 558/272

*Primary Examiner*—Patricia L. Morris
*Assistant Examiner*—Michael G. Ambrose
*Attorney, Agent, or Firm*—Nixon & Vanderhye

[57] ABSTRACT

Disclosed are fluorobenzene derivatives, which are important intermediates for producing herbicidal oxazolidinedione derivatives, and methods of producing them. The fluorobenzene derivatives include compounds of a formula (11):

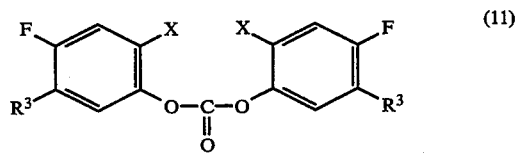

where X is a halogen atom, $R^3$ is a nitro, amino or isocyanato group or $R^1OCONH$, and $R^1$ is an alkyl or phenyl group. Via the intermediates of the invention, oxazolidinedione derivatives can be produced with high yield.

2 Claims, No Drawings

FLUOROBENZENE DERIVATIVES

This is a division of application Ser. No. 07/823,454, filed Jan. 21, 1992, now U.S. Pat. No. 5,281,742.

BACKGROUND OF THE INVENTION

1. Field of the Invention

The present invention relates to novel intermediates for producing oxazolidinedione derivatives of a formula (13):

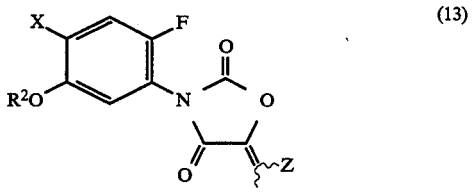

where X represents a halogen atom; $R^2$ represents a cycloalkyl group having from 3 to 8 carbon atoms, or an alkynyl group having from 3 to 5 carbon atoms, the cycloalkyl group being either substituted or unsubstituted; and Z represents a methyl group, or an ethyl group; the derivatives being used as an active ingredient for herbicides; as well as to methods of preparing them.

More precisely, the present invention relates to diphenylcarbonate derivatives of a formula (11):

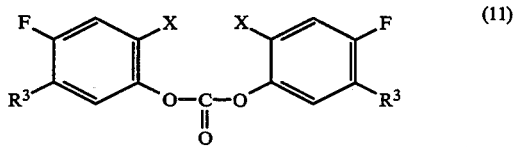

where X represents a halogen atom; $R^3$ represents a nitro group, an amino group, an isocyanato group, or $R^1OCONH$; and $R^1$ in $R^1OCONH$ represents an alkyl group having from 1 to 8 carbon atoms, or a phenyl group, the alkyl group being either substituted or unsubstituted; and phenylcarbamate derivatives of a formula (12):

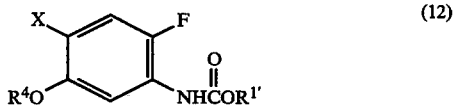

where X represents a halogen atom; $R^{1'}$ represents an alkyl group having from 1 to 8 carbon atoms, a phenyl group, or a benzyl group; $R^4$ represents a hydrogen atom, a cycloalkyl group having from 3 to 8 carbon atoms, or an alkynyl group having from 3 to 5 carbon atoms, the cycloalkyl group being either substituted or unsubstituted; as well as to methods of preparing them.

PRIOR ART

Oxazolidinedione derivatives of formula (13) are compounds having an extremely excellent herbicidal activity. (Refer to Japanese Patent Application Laid-Open Nos. 62-167713 and 2-25405.) As methods of preparing them, those described in Japanese Patent Application Laid-Open Nos. 62-174065 and 3-178957 are known. However, the known methods are not always satisfactory in point of the purity and yield of the products. No method of simply preparing oxazolidinedione derivatives via diphenylcarbonate derivatives or phenylcarbamate derivatives has ever been developed.

SUMMARY OF THE INVENTION

The present inventors investigated methods of industrially advantageously producing oxazolidinedione derivatives of formula (13) and, as a result, have found that oxazolidinedione derivatives of the kind can be produced with high yield when diphenylcarbonate derivatives of formula (11) and phenylcarbamate derivatives of formula (12) are used.

In accordance with the present invention, therefore, there are provided novel diphenylcarbonate derivatives and novel phenylcarbamate derivatives of the above-mentioned formulae (11) and (12), respectively.

DETAILED DESCRIPTION OF THE INVENTION

Diphenylcarbonate derivatives and phenylcarbamate derivatives of the present invention, which are represented by formulae (11) and (12), respectively, can be produced in accordance with the reaction routes mentioned below.

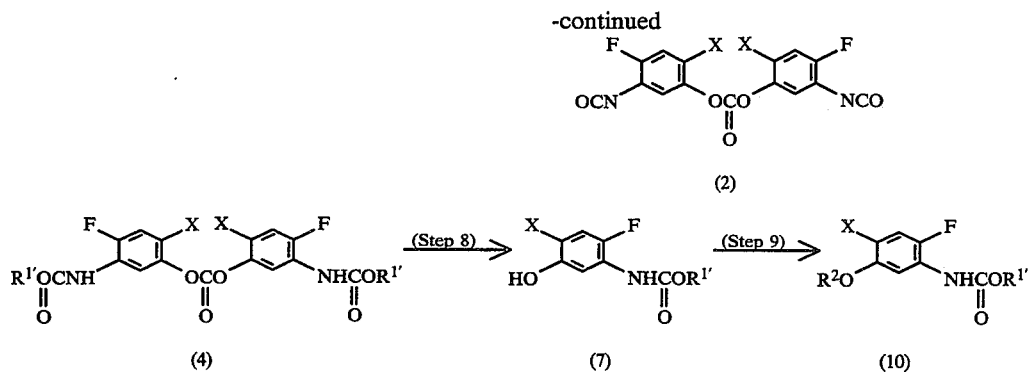

In the above-mentioned reaction routes, X represents a halogen atom; $R^1$ represents an alkyl group having from 1 to 8 carbon atoms, or a phenyl group; $R^{1'}$ represents an alkyl group having from 1 to 8 carbon atoms, a phenyl group, or a benzyl group; $R^2$ represents a cycloalkyl group having from 3 to 8 carbon atoms, or an alkynyl group having from 3 to 5 carbon atoms. The alkyl group to be represented by $R^1$ and the cycloalkyl group to be represented by $R^2$ may be either substituted or unsubstituted.

(Step 1) is a step of halogenating a known compound 4-fluorophenol (14) by a known method (U.S. Pat No. 5,053,557) to convert it into a 2-halogeno-4-fluorophenol (15). For instance, where X is a chlorine atom, 4-fluorophenol may be reacted with one equivalent of chlorine gas or with from 1 to 2 equivalents of sulfuryl chloride in an aqueous solvent at 60° to 70° C., to give 2-chloro-4-fluorophenol.

(Step 2) is a step of reacting the 2-halogeno-4-fluorophenol (15) with phosgene or its analogue to convert it into a bis(2-halogeno-4-fluorophenyl)carbonate (16). In general, the reaction is effected in a two-layer reaction system composed of an organic solvent and water in the presence of a base and phosgene or a phosgene analogue is introduced into the reaction system at a low temperature, whereby the phenol (15) is converted into the carbonate (16). Phosgene is used in an amount of 0.5 equivalent or more to the 2-halogeno-4-fluorophenol to obtain the intended bis (2-halogeno-4-fluorophenyl)carbonate in high yield. As the base, usable is an alkali metal hydroxide such as sodium hydroxide or potassium hydroxide. The amount of the base to be used is preferably one equivalent or more to the substrate in view of the yield of the product. As the organic solvent to be used for the reaction, there are mentioned, for example methylene chloride, chloroform, ethyl acetate, benzene and toluene.

In preparing the diphenylcarbonates, a phase transfer catalyst such as quaternary ammonium salts may be added to the reaction system so as to more rapidly promote the reaction. As usable quaternary ammonium salts for the purpose, there are mentioned, for example, triethylbenzylammonium chloride, tetrabutylammonium chloride, cetyltrimethylammonium chloride, trioctylmethylammonium chloride, and the corresponding bromides, and trimethylbenzylammonium hydroxide.

(Step 3) is a step of reacting the bis(2-halogeno-4-fluorophenyl)carbonate (16) with a mixed acid as prepared from nitric acid and sulfuric acid, in a solvent of sulfuric acid, to convert it into a bis(2-halogeno-4-fluoro-5-nitrophenyl)carbonate (5) in high yield. The concentration of the sulfuric acid as a solvent is not specifically defined, and an ordinary commercial product of 95 to 98 wt. % sulfuric acid may be used. The amount of the sulfuric acid solvent may be from 1 to 30 equivalents, preferably from 5 to 15 equivalents, to the substrate, whereupon the product can be obtained in high yield. As nitric acid and sulfuric acid to be used in preparing the mixed acid, ordinary commercial products of 60 to 71 wt. % nitric acid and 95 to 98 wt % sulfuric acid can be used to obtain the nitrated product in high yield. The molar ratio of nitric acid to sulfuric acid in the mixed acid may be from 2/1 to ¼, preferably from 1/1 to ¼, as nitric acid/sulfuric acid; and the amount of nitric acid to be used may be from 2 to 10 equivalents, preferably from 2 to 5 equivalents, to the substrate, to obtain the intended product in high yield. The reaction temperature may be selected from the range of from −10° C. to 80° C. Preferably, the reaction is effected at a low temperature ranging from 0° C. to 30° C., in point of the yield of the product and the safety of the reaction system.

Hitherto, for producing bis(polyhalonitrophenyl)carbonates by nitration of a polyhalodiphenylcarbonate, there have been known (a) a method of using a mixed acid composed of nitric acid and sulfuric acid (Japanese Patent Publication No. 49-10661) and (b) a method of using a fuming nitric acid (Japanese Patent Kohyo Koho No. 61-500069). However, both the known methods are defective in that the former method (a) needs a high reaction temperature and the latter method (b) must use a dangerous fuming nitric acid, and they could not be said to be industrially convenient methods.

Although bis(2-chloro-4-fluoro-5-nitrophenyl)carbonate of a compound of the present invention is described in Japanese Patent Application Laid-Open No. 1-163157 as a starting compound, the publication has neither disclosure of illustrating an example of producing the compound nor disclosure of indicating the physical data and spectral data of the compound. Regarding the method of producing the compound, the publication mentions that the compound can be obtained by nitrating the corresponding starting compound with nitric acid. However, as a result of filtration of bis(2-chloro-4-fluorophenyl)carbonate as effected by the present inventors, bis(2-chloro-4-fluoro-5-nitrophenyl)carbonate could not be obtained. (Refer to Examples 4 to 6 and Referential Example 1 to follow hereunder).

(Step 4) is a step of reducing the nitro group of the bis(2-halogeno-4-fluoro-5-nitrophenyl)carbonate (5) in an organic solvent so as to convert the carbonate (5) into a bis(2-halogeno-4-fluoro-5-aminophenyl)carbonate (1). The reaction may be effected by a method which is generally used for reduction of an aromatic nitro compound. For instance, usable are a method of using reduced iron/acetic acid, reduced iron/hydrochloric acid, zinc/hydrochloric acid, or sodium sulfide; and a catalytic reduction method of using a transition metal catalyst such as Pd/C, Pd-black, Pd-asbestos, Pd-alumina, PtO$_2$ or Pt-black. The amount of the catalyst to be used in the catalytic reduction method is not specifically defined, but it may be from 0.0001 to 0.5 equivalent, preferably from 0.005 to 0.05 equivalent, to the substrate, to obtain the intended product with high yield. As an organic solvent usable in the reaction, there are mentioned, for example, aromatic solvents such as benzene, chlorobenzene, dichlorobenzene and toluene, as well as alcohol solvents such as methanol and ethanol. The reaction temperature may be from room temperature to approximately 100° C.

(Step 5) is a step of converting the bis(2-halogeno-4-fluoro-5-aminophenyl)carbonate (1) into a bis(2-halogeno-4-fluoro-5-isocyanatophenyl)carbonate (2). The reaction is effected, for example, with phosgene or a phosgene analogue. The reaction may conducted in an organic solvent. Any and every organic solvent which does not have any harmful influence on the reaction may be used in the reaction. As usable solvents, for example, there are mentioned ethyl acetate, chloroform, acetonitrile, acetone, toluene, benzene and chlorobenzene. The reaction may be effected, for example, by gradually dropwise adding a solution of a bis(2-halogeno-4-fluoro-5-aminophenyl)carbonate to a solution of phosgene or a phosgene analogue at a lowered temperature to room temperature; or by gradually adding phosgene or a phosgene analogue as it is or as a solution thereof to a solution of a bis(2-halogeno-4-fluoro-5-aminophenyl)carbonate at a lowered temperature to room temperature. Next, the reactants are reacted with each other at room temperature to a temperature of approximately 100° C. to obtain the corresponding isocyanato derivative. The amount of the phosgene or phosgene analogue to be used in the reaction is not specifically defined. It may be 2 equivalents or more, as phosgene, to the aniline derivative, whereby the intended isocyanate derivative may be obtained in high yield.

(Step 6) is a step of converting the bis(2-halogeno-4-fluoro-5-isocyanatophenyl)carbonate (2) into a diphenylcarbonate derivative (4). The reaction may be effected by reacting the bis(2-halogeno-4-fluoro-5-isocyanatophenyl)carbonate (2) with an alcohol of a formula:

R$^1$OH (3)

where R$^1$ has the same meaning as mentioned above, in the presence of a base. The reaction may be carried out in the absence of a solvent or may be carried out in the presence of an organic solvent. As examples of usable organic solvents, there are mentioned ethers such as diethyl ether, tetrahydrofuran, dioxane and dimethoxyethane; aromatic solvents such as benzene, toluene and xylene; as well as acetonitrile, acetone, methyl ethyl ketone, N,N-dimethylformamide and dimethylsulfoxide. The reaction is preferably effected in the presence of a base in view of the rapid reaction rate and the high yield of the product. As bases usable in the reaction, there are mentioned, for example, amines such as triethylamine, tributylamine, N-methylmorpholine, N,N-dimethylaniline, N,N-diethylaniline, pyridine and lutidine; and alkali metal salts such as potassium carbonate, sodium carbonate, sodium methoxide and potassium t-butoxide. The amount of the base to be used in the reaction is not specifically defined, and it may well be a catalytic amount. The reaction may well be conducted at a low temperature. After the reaction, the reaction mixture may be subjected to any conventional post-treatment to obtain the intended product in high yield.

(Step 7) is a step of reacting the bis(2-halogeno-4-fluoro-5-aminophenyl)carbonate (1) with a chloroformate of a formula (6):

ClCOOR$^1$ (6)

where R$^1$ has the same meaning as mentioned above, in the presence of a base, so as to convert the carbonate (1) into a diphenylcarbonate derivative of formula (4).

The reaction may be effected in an organic solvent. As usable solvents, for example, there are mentioned ethers such as diethyl ether, tetrahydrofuran, dioxane and dimethoxyethane; ketones such as acetone and methyl ethyl ketone; aromatic solvents such as benzene, toluene and xylene; as well as ethyl acetate, acetonitrile and dimethylsulfoxide. The reaction is carried out in the presence of a base. As usable bases, there are mentioned, for example, amines such as triethylamine, tributylamine, N-methylmorpholine, N,N-dimethylaniline, N,N-diethylaniline, pyridine and lutidine; and alkali metal salts such as potassium carbonate, sodium carbonate, sodium methoxide and potassium t-butoxide. The base is used in the reaction preferably in an amount not less than the stoichiometric amount to the substrate, whereby the reaction may be completed in a short period of time and the yield of the product to be obtained by the reaction is high.

As the starting material chloroformate (6) for the reaction, a commercial product may directly be employed as it is, or a product to be obtained with ease from phosgene or its analogue and an alcohol may also be employed. As alcohols to be used for producing the chloroformate (6), there are mentioned, for example, methanol, ethanol, propyl alcohol, isopropyl alcohol, allyl alcohol, phenol and benzyl alcohol. As examples of chloroformates of formula (6) including commercial products, there are mentioned methyl chloroformate, ethyl chloroformate, propyl chloroformate, allyl chloroformate, crotyl chloroformate, phenyl chloroformate and benzyl chloroformate.

(Step 8) is a step of selectively hydrolyzing only the carbonate moiety of the diphenylcarbonate derivative of formula (4) in a protonic solvent in the presence of a base so as to convert the derivative (4) into a phenylcarbamate derivative of formula (7). Inorganic bases are usable in the reaction, including, for example, sodium carbonate, potassium carbonate, sodium hydrogencarbonate, potassium hydrogencarbonate, sodium hydroxide, potassium hydroxide and calcium hydroxide. As usable protonic solvents, there are mentioned, for example, water, acetic acid, as well as alcoholic solvents such as methanol, ethanol and isopropyl alcohol, and mixed solvents of any two or more of them. In addition, also usable are other mixed solvents composed of any of the said solvents and any of other organic solvents such as acetone, methyl ethyl ketone, acetonitrile, tetrahydrofuran and N,N-dimethylformamide. The reaction may be effected with ease at room temperature, and, if desired, it may be completed in a short period of time by heating the reaction system. The amount of the base to be used in the reaction may be generally from 0.01 to 5.0 equivalents, preferably from 0.1 to 2.0 equivalents, as the metal, to one equivalent of the diphenylcarbonate derivative (4). After completion of the reaction, the reaction mixture is added to an aqueous hydrochloric acid solution, whereupon the crystals as precipitated out are isolated by filtration; or alternatively, the product is extracted out with an organic solvent from the reaction mixture. The thus isolated product is then subjected to ordinary treatment such as drying and concentration to obtain the intended phenylcarbamate derivative (7).

(Step 9) is a step of reacting the phenylcarbamate derivative of formula (7) with a compound of a formula (9):

$$R^2Y \qquad (9)$$

where $R^2$ has the same meaning as mentioned above and Y represents a leaving group, in the presence of a base, so as to convert the derivative (7) into a phenylcarbamate derivative (10).

The reaction is effected in the presence of a base. As usable bases, there are mentioned alkali metal carbonates such as sodium carbonate and potassium carbonate; alkyl lithium reagents such as butyl lithium and methyl lithium; as well as sodium amide and sodium hydroxide. The reaction is preferably effected in an organic solvent. As usable organic solvents, there are mentioned acetone, methyl ethyl ketone, acetonitrile, ether, tetrahydrofuran, N,N-dimethylformamide, toluene, benzene, and mixed solvents of any two or more of them. The reaction temperature varies, depending upon the base to be used. The reaction may well be carried out even at room temperature, and it may be completed in a short period of time by heating the reaction system.

The cycloalkyl group in formula (9) includes, for example, cyclopropyl, cyclopentyl, 3-methylcyclopentyl, 2-methylcyclopentyl and cyclohexyl groups. The alkynyl group in the same includes, for example, propargyl, 1-butyn-3-yl and 3-butyl-1-yl groups. As examples of the leaving group of Y, there are mentioned a halogen atom such as iodine and bromine atoms; and a sulfonyloxy group such as p-toluenesulfonyloxy, phenylsulfonyloxy and methylsulfonyloxy, trifluoromethylsulfonyloxy groups.

As compounds of formula (9), commercial halides may directly be used as they are. Alternatively, an alcohol is reacted with a sulfonic acid chloride such as benzenesulfonyl chloride, p-toluenesulfonyl chloride, methanesulfonyl chloride or trifluoromethanesulfonyl chloride, to give a sulfonate, and the resulting sulfonate may also be used in the reaction. Therefore, as examples of compounds of formula (9) including commercial products, there are mentioned cyclopropyl bromide, cyclopentyl bromide, cyclohexyl bromide, propargyl bromide, 3-bromo-1-butyne, 1-bromo-3-pentyne, cyclopentyl benzenesulfonate, cyclopentyl p-toluenesulfonate, 3-methylcyclopentyl p-toluenesulfonate, 2-methylcyclopentyl p-toluenesulfonate, cyclopentyl methanesulfonate, cyclohexyl p-toluenesulfonate, propargyl p-toluenesulfonate, propargyl trifluoromethanesulfonate, 1-butyn-3-yl p-toluenesulfonate, 1-butyn-3-yl trifluoromethanesulfonate, and 1-butyn-3-yl methanesulfonate.

In general, the amount of the compound of formula (9) to be used in the reaction is from 1.0 to 2.0 equivalents, preferably from 1.1 to 1.2 equivalents, to one equivalent of the phenylcarbamate derivative (7); and that of the base to be used in the same is from 1.0 to 3.0 equivalents, preferably from 1.0 to 2.0 equivalents, as the metal, to one equivalent of the phenylcarbamate derivative (7). After the reaction, the reaction mixture is added to an aqueous acid solution, whereupon the crystals as precipitated out are isolated by filtration; or the product formed is extracted out with an organic solvent from the reaction mixture. The product thus isolated or extracted is then subjected to an ordinary treatment such as drying or concentration to obtain the intended phenylcarbamate derivative (10). The reaction of (Step 9) may be effected in the presence of a catalyst. As usable catalysts, there are mentioned alkali metal halides such as sodium bromide, potassium bromide, sodium iodide and potassium iodide. The amount of the catalyst to be used may be generally from 0.001 to 0.5 equivalents to the phenylcarbamate derivative (7), whereby the reaction may well be promoted.

(Step 7), (Step 8) and (Step 9) may be conducted successively in order or simultaneously at the same time in a same reactor, whereupon the phenylcarbamate derivative (9) may directly be obtained from the diphenylcarbonate derivative (1) without isolating the diphenylcarbonate derivative (4) and the phenylcarbamate derivative (7). Precisely, a diphenylcarbonate derivative (1) is reacted with a chloroformate of formula (6) in the presence of an alkali metal, as a base, to give a carbamate derivative (4), then a protonic solvent necessary for hydrolyzing the carbonate group of the derivative (4) is added thereto so as to hydrolyze only the carbonate group thereof, and the resulting alkali metal phenoxide of a phenylcarbamate derivative (7) is reacted with a compound of formula (9) successively in order or simultaneously at the same time to obtain a phenylcarbamate derivative (10).

The reaction is desired to be effected in the solvent as referred to for the above-mentioned (Step 7) to (Step 9). For instance, acetone, methyl ethyl ketone or toluene may be used as the solvent. The reaction is carried out at a temperature of from room temperature to the boiling point of the solvent used, preferably from room temperature to 80° C.

Compounds of formulae (1), (2) and (4) produced in the above-mentioned reaction routes are novel compounds. A compound of formula (5) where X is Cl is referred to in the above-mentioned publication, but it could not be produced by the method described in the same. In addition, since the publication does not refer to the physical data of the compound, the compound may be said to be a novel compound.

Novel compounds of formulae (1), (2), (4) and (5) can be represented by a general formula (11):

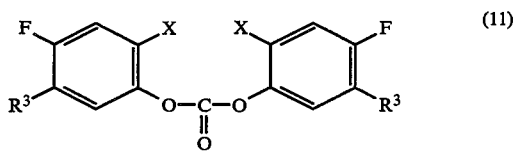

where $R^3$ represents a nitro group, an amino group, an isocyanato group, or $R^1OCONH$; and $R^1$ represents a substituted or unsubstituted alkyl group having from 1 to 8 carbon atoms, or phenyl group.

More precisely, $R^1$ represents a linear or branched alkyl group, such as methyl group, ethyl group, propyl group, isopropyl group, butyl group, isobutyl group, sec-butyl group, t-butyl group, hexyl group, octyl group or 2-ethylhexyl group. The alkyl group may optionally be substituted by substituent(s) selected from a phenyl group, a substituted or unsubstituted vinyl group, an alkoxycarbonyl group in which the alkyl moiety has from 1 to 4 carbon atoms, and a halogen atom. As examples of the substituted alkyl group, there are mentioned benzyl group, allyl group, methallyl group, crotyl group, 1-methoxycarbonyl-2-methyl-2-propenyl group, 1-ethoxycarbonyl-2-mehtyl-2-propenyl group, 1-propyloxycarbonyl-2-methyl-2-propenyl group, 1-butoxycarbonyl-2-methyl-2-propenyl group, 1-methoxycarbonyl-2-ethyl-2-propenyl group, 1-methoxycarbonyl-2-methyl-2-butenyl group, 1-methoxy-carbonyl-2-ethyl-2-butenyl group, 1-ethoxycarbonyl-2-phenyl-2-propenyl group, 2,2,2-trifluoroethyl group and 3-fluoropropyl group. X represents fluorine, chlorine, bromine or iodine atom.

More concretely, as examples of the compounds of the present invention, there are mentioned bis(2-chloro-4-fluoro-5-aminophenyl) carbonate, bis (2-chloro-4-fluoro-5-isocyanatophenyl) carbonate, bis{2-chloro-4-fluoro-5-(methoxycarbonylamino)phenyl}carbonate, bis{2-chloro-4-fluoro-5-(ethoxycarbonylamino)phenyl} carbonate, bis{2-chloro-4-fluoro-5-(propyloxycarbonylamino)phenyl}carbonate, bis{2-chloro-4-fluoro-5-(isopropyloxycarbonylamino)phenyl}carbonate, bis{2-chloro-4-fluoro-5-(butoxycarbonylamino)phenyl}carbonate, bis{2-chloro-4-fluoro-5-(2-ethylhexyl)oxycarbonylamino)phenyl}carbonate, bis{2-chloro-4-fluoro-5-(phenoxycarbonylamino)phenyl}carbonate, bis{2-chloro-4-fluoro-5-(benzyloxycarbonylamino)phenyl} carbonate, bis[2-chloro-4-fluoro-5-{(2,2,2-trifluoroethyl)oxycarbonylamino}phenyl]carbonate, bis[2-chloro-4-fluoro-5-{(3-fluoropropyl)oxycarbonylamino} phenyl]carbonate, bis{2-chloro-4-fluoro-5-(allyloxycarbonylamino)phenyl}carbonate, bis{2-chloro-4-fluoro-5-(methallyloxycarbonylamino)phenyl]carbonate, bis{2-chloro-4-fluoro-5-(crotyloxycarbonylamino)phenyl} carbonate, bis[2-chloro-4-fluoro-5-{(1-methoxycarbonyl-2-methyl-2-propenyl)oxycarbonylamino}phenyl]carbonate, bis[2-chloro-4-fluoro-5-{(1-ethoxycarbonyl-2-methyl-2-propenyl)oxycarbonylamino}phenyl]carbonate, bis[2-chloro-4-fluoro-5-{(1-butoxycarbonyl-2-methyl-2-propenyl)oxycarbonylamino}phenyl]carbonate, bis[2-chloro-4-fluoro-5-{(1-methoxycarbonyl-2-methyl-2-butenyl)oxycarbonylamino}phenyl]carbonate, and bis[2-chloro-4-fluoro-5-{(1-ethoxycarbonyl-2-methyl-2-butenyl)oxycarbonylamino}phenyl]carbonate.

Novel compounds of formulae (7) and (10) can be represented by a general formula (12):

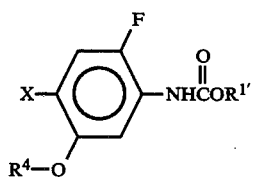

(12)

In formula (12), X and $R^{1'}$ have the same meanings as mentioned above. $R^4$ represents a hydrogen atom, a cycloalkyl group having from 3 to 8 carbon atoms, or an alkynyl group having from 3 to 5 carbon atoms. As examples of the cycloalkyl group having from 3 to 8 carbon atoms, there are mentioned cyclopropyl group, cyclopentyl group and cyclohexyl group. The cycloalkyl group may optionally be substituted by substituent(s) selected from a lower alkyl group having from 1 to 4 carbon atoms, and a halogen atom. As examples of the substituted cycloalkyl group, there are mentioned 3-methylcyclopentyl group, 2-methylcyclopentyl group, 2-chlorocyclopentyl group and 2-methylcyclopentyl group. As examples of the alkynyl group having from 3 to 5 carbon atoms, there are mentioned propargyl group, 1-butyn-3-yl group, 3-butyn-1-yl group and 3-pentyn-1-yl group.

More concretely, as examples of the compounds of the present invention, there are mentioned methyl N-(2-fluoro-4-chloro-5-cyclopentyloxyphenyl)carbamate, ethyl N-(2-fluoro-4-chloro-5-cyclopentyloxyphenyl)carbamate, isobutyl N-(2-fluoro-4-chloro-5-cyclopentyloxyphenyl)carbamate, methyl N-{2-fluoro-4-chloro-5-(3-methylcyclopentyl)oxyphenyl}carbamate, methyl N-{2-fluoro-4-chloro-5-(2methylcyclopentyl)oxyphenyl}carbamate, methyl N-(2-fluoro-4-chloro-5-cyclohexyloxyphenyl)carbamate, phenyl N-(2-fluoro-4-chloro-5-cyclopentyloxyphenyl)carbamate, benzyl N-(2-fluoro-4-chloro-5-cyclopentyloxyphenyl)carbamate, methyl N-(2-fluoro-4-chloro-5-propargyloxyphenyl)carbamate, methyl N-{2-fluoro-4-chloro-5-(3-butyn-1-yl)oxyphenyl}carbamate, and ethyl N-{2-fluoro-4-chloro-5-(3-butyn-1-yl)oxyphenyl}carbamate.

The phenylcarbamate derivative (10) of the present invention thus prepared can be led into an oxazolidine derivative of a formula (13) having an herbicidal activity, in accordance with the reaction route mentioned below.

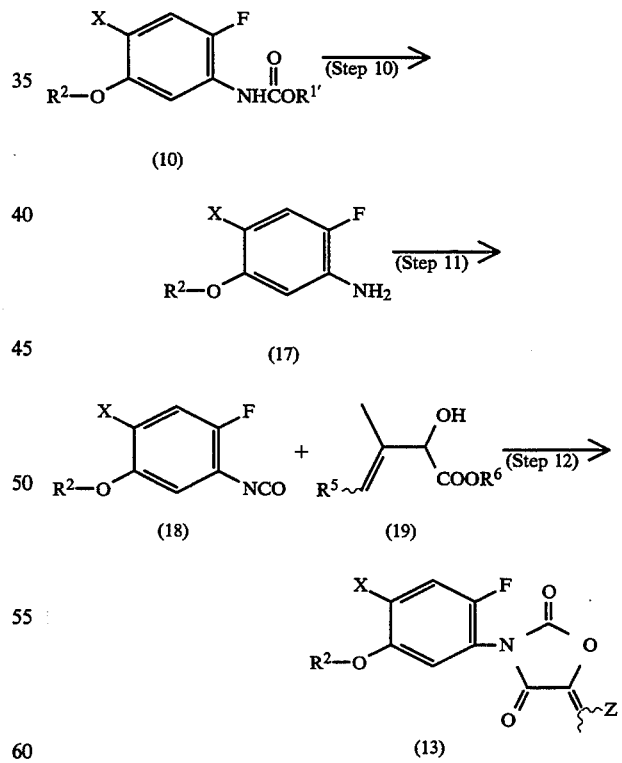

In these formulae, X, $R^{1'}$, $R^2$ and Z have the same meanings as mentioned above; $R^5$ represents a hydrogen atom or a methyl group; and $R^6$ represents a lower alkyl group having from 1 to 4 carbon atoms.

(Step 10) is a step of hydrolyzing the N-(substituted phenyl)carbamate (10) to obtain an aniline derivative (17). The reaction is preferably effected in the presence of a base, which may be an aqueous solution of a metal hydroxide such as sodium hydroxide, potassium hydroxide or calcium hydroxide, in a mixed solvent containing an alcoholic solvent such as methanol, ethanol or isopropyl alcohol in view of the yield of the product.

(Step 11) is a step of converting the amino group of the aniline derivative (17) into an isocyanato group with phosgene or a phosgene analogue to obtain a phenylisocyanate derivative (18). The reaction may be effected in an organic solvent. Solvents usable in the reaction are ethyl acetate, benzene and toluene. The reaction may be conducted by introducing a solution of the aniline derivative (17) into a solution of phosgene or a phosgene analogue; or alternatively, by adding phosgene or a phosgene analogue to a solution of the aniline derivative (17). During addition of the reactants, the reaction is conducted at a low temperature not higher than room temperature, and thereafter the reaction mixture are heated up to about 100° C. to finish the reaction. After the reaction, the solvent was removed by distillation, whereby the intended product isocyanate derivative (10) may be obtained in high yield.

(Step 12) is a step of reacting the isocyanate derivative (18) obtained in (Step 11) with a 2-hydroxyglycolate (19) in the presence of a base to obtain a 3N-(2-fluoro-4-halogeno-5-alkoxyphenyl)-5-alkylidene-1,3-oxazolidine-2,4-dione (13), which is an active ingredient of a herbicide. The reaction is effected in an organic solvent in the presence of a base, for example, an amine such as triethylamine, tributylamine, N-methylmorpholine, pyridine or N,N-dimethylaniline, or an alkali metal carbonate such as potassium carbonate or sodium carbonate, or a mixture of them. The amount of the base to be used in the reaction is not specifically defined, and it may well be a catalytic amount. As usable organic solvents, there are mentioned toluene, benzene, ethyl acetate, acetone, acetonitrile, tetrahydrofuran and N,N-dimethylformamide. The reaction may be effected at room temperature, depending upon the kind of the solvent used. Preferably, it is effected at a temperature falling within the range of from room temperature to the refluxing temperature of the solvent used, so as to shorten the reaction time.

Of the compounds of formula (4) of the present invention, a diphenylcarbonate derivative (20) where $R^{1''}$ is a 1-(lower alkoxycarbonyl)-2-methyl-2-propenyl group or a 1-(lower alkoxycarbonyl)-2-methyl-2-butenyl group can be converted into a final product (13), via a 3N-(2-fluoro-4-halogeno-5-hydroxyphenyl)-5-alkylidene-1,3-oxazolidine-2,4-dione (8) which is an important intermediate for preparing the active ingredient (13) of a herbicide, in accordance with the reaction route mentioned below.

In these formulae, X, Y, Z, $R^2$, $R^5$ and $R^6$ have the same meanings mentioned above.

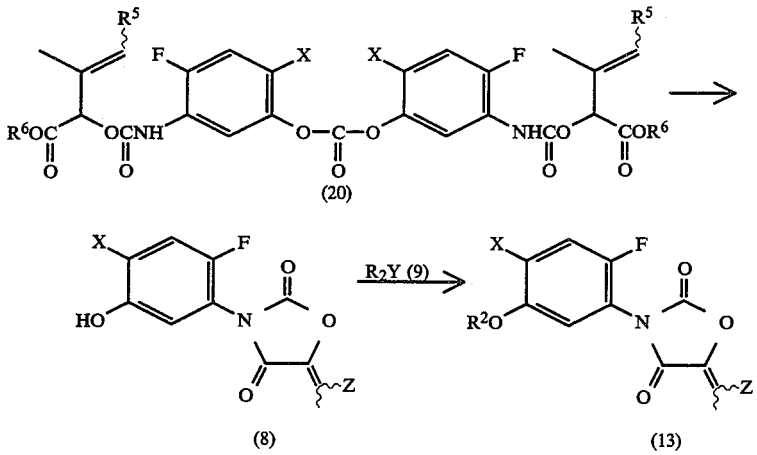

For instance, bis[2-chloro-4-fluoro-5-{(1-ethoxycarbonyl-2-methyl-2-propenyl)oxycarbonylamino}phenyl]carbonate, which is a compound of the present invention, is treated with a base in a protonic solvent to effect intramolecular cyclization of the compound and the successive hydrolysis of the carbonate bond thereof at the same time, whereby the carbonate is converted into 3N-(2-fluoro-4-chloro-5-hydroxyphenyl)-5-isopropylidene-1,3-oxazolidine-2,4-dione which is an important intermediate for preparing an active ingredient of a herbicide. As the protonic solvent for the reaction, usable are alcohols such as methanol, ethanol and isopropyl alcohol, carboxylic acids such as acetic acid and propionic acid, and water. As the case may be, a mixed solvent composed of any of the said protonic solvents and any of other organic solvents such as acetone, acetonitrile, tetrahydrofuran and N,N-dimethylformamide may also be used in carrying out the reaction. The reaction is effected in the presence of a base, which may be selected from amines such as triethylamine, tributylamine, N-methylmorpholine and N,N-dimethylaniline, and alkali metal salts such as potassium carbonate, sodium carbonate and sodium methoxide. The amount of the base to be used in the reaction system is not specifically defined, but it is preferably one equivalent or more to the substrate in order to finish the reaction in a short period of time and to elevate the yield of the product.

3N-(2-fluoro-4-chloro-5-hydroxyphenyl)-5-isopropylidene-1,3-oxazolidine-2,4-dione thus obtained is reacted with an electrophile of formula (9) in an organic solvent such as acetone, methyl ethyl ketone, acetonitrile or N,N-dimethylformamide, in the presence of a base such as potassium carbonate or sodium carbonate, whereby it is converted with ease into an oxazolidinedione derivative of formula (13).

Next, the present invention will be explained in more detail by way of the following examples and comparative examples, which, however, are not intended to restrict the scope of the present invention.

EXAMPLE 1:

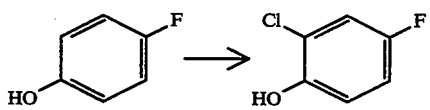

4-Fluorophenol (44.8 g, 0.40 mol) and water (80 ml) were added to a 200-ml three-neck flask as equipped with a stirrer and a dropping funnel, and sulfuryl chloride (60 ml, 100 g, 0.47 mol) was dropwise added thereto over a period of 60 minutes with the reaction system being kept at 60° to 70° C. After completion of the reaction, saturated brine (400 ml) was added to the reaction system, which was then extracted with methylene chloride (200 ml×3). The organic layer was dried with anhydrous magnesium sulfate. After the drying agent was removed, the solvent was removed by distillation under reduced pressure to obtain a crude product (56.4 g). The composition of the product comprised 2-chloro-4-fluorophenol (97.6%), 2,6-dichloro-4-fluorophenol (1.0%) and unreacted starting materials (0.7%), and it contained no other higher order chlorides.

$^1$H-NMR(CDCl$_3$): δ 5.60 (1H, s), 6.9~7.3 (3H, m) ppm.

EXAMPLE 2:

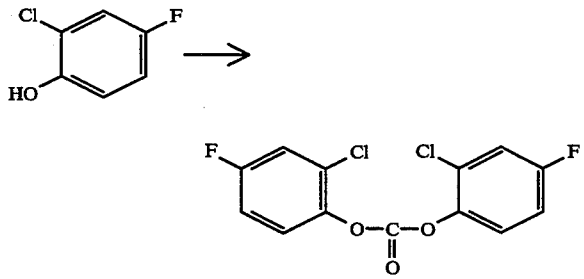

2-Chloro-4-fluorophenol (733 g, 5.0 mol) and methylene chloride (2.5 liters) were put in a 5-liter three-neck flask as equipped with a stirrer, and 4N sodium hydroxide aqueous solution (1350 ml) was added thereto and stirred with cooling. To the resulting solution was introduced phosgene as generated by decomposing trichloromethyl chloroformate (148 ml, 243 g, 1.23 mol) on an active charcoal (3.8 g) at a temperature of 40° to 50° C. After introduction of phosgene, the reaction solution was further stirred overnight at room temperature. After the reaction, the organic layer was separated, and the aqueous layer was extracted with methylene chloride (500 ml×2). The organic layers were combined, washed with 1N sodium hydroxide aqueous solution (1000 ml) and water, and thereafter dried with anhydrous magnesium sulfate. The drying agent was removed, and the solvent was removed by distillation under reduced pressure to obtain a white solid of bis(2-chloro-4-fluorophenyl)carbonate (801 g, 5.0 mol). Yield: 100%.

m.p.: 91.0° to 92.0° C.

$^1$H-NMR(CDCl$_3$): δ 6.87~7.4 (6H, m) ppm.

IR (KBr disk): 1780, 1605, 1500, 1290, 1250, 1180 cm$^{-1}$.

EXAMPLE 3:

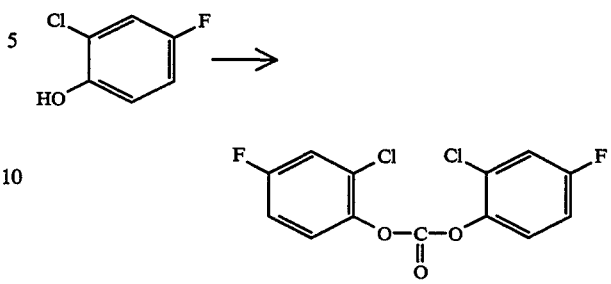

2-Chloro-4-fluorophenol (4.4 kg, 30 mol), triethylbenzylammonium chloride (17.1 g) and methylene chloride (7 liters) were put in a 20-liter three-neck flask as equipped with a stirrer and a dropping funnel, and cooled in an ice-water bath. 5N sodium hydroxide aqueous solution (6 liters) was gradually added thereto with stirring vigorously. Next, trichloromethyl chloroformate (885 ml, 7.35 mol) was gradually dropwise added thereto over a period of about 6 hours. After addition, the reaction liquid was stirred overnight. After reaction, the organic layer was separated, and the aqueous layer was extracted with methylene chloride (1000 ml×2). The organic layers were combined, washed with 1N sodium hydroxide aqueous solution (4 liters) and water (5 liters) and then dried with anhydrous magnesium sulfate. The drying agent was taken out by filtration, and the solvent was removed from the organic layer by distillation under reduced pressure to obtain a white solid of bis(2-chloro-4-fluorophenyl)carbonate (4.9 kg, 5.4 mol). Yield: 100%. Spectral data and other data of the product are those as shown in Example 2.

EXAMPLE 4:

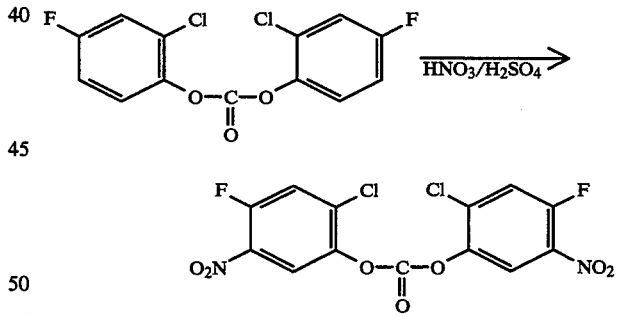

Bis(2-chloro-4-fluorophenyl)carbonate (801 g, 2.5 mol) was put in a 5-liter three-neck flask as equipped with a stirrer and a dropping funnel, and sulfuric acid (98%, 2000 ml) was added thereto with stirring well. Next, a mixed acid as prepared from nitric acid (60%, 400 ml) and sulfuric acid (98%, 400 ml) was gradually dropwise added thereto through the dropping funnel, with vigorously stirring over a period of 7 hours, in such a way that the reaction temperature did not rise. After addition, the whole was stirred vigorously for further one hour and thereafter it was poured into a cold water (5000 ml), whereupon the white solid as precipitated out was taken out by filtration, washed with water and well dried to obtain bis(2-chloro-4-fluoro-5-nitrophenyl)carbonate (1026 g, 2.5 mol) as a white solid product. Yield: 100%. This was recrystallized from toluene or ethyl acetate and was isolated as a pure white needle-like crystal.

m.p.: 165.0° to 165.5° C.

$^1$H-NMR(CDCl$_3$): δ 7.58 (2H, d, $J_{HF}$=9.9 Hz), 8.25 (2H, d, $J_{HF}$=8.3 Hz) ppm.

IR (KBr disk): 1797, 1605, 1540, 1495, 1355, 1240, 1180 cm$^{-1}$.

Elementary Analysis (%, C$_{13}$H$_4$Cl$_2$F$_2$N$_2$O$_7$, molecular weight: 409,084)

Calculated: C=38.17, H=0.99, N=6.85
Measured: C=38.16, H=0.69 N=6.65

EXAMPLE 5:

Bis(2-chloro-4-fluorophenyl)carbonate (15.3 g, 48.0 mmol) was put in a 100-ml three-neck flask as equipped with a dropping funnel and a stirrer, and sulfuric acid (98%, 30 ml) was added thereto with cooling in an ice-water bath with fully stirring. Next, a mixed acid as prepared from nitric acid (60%, 17 ml) and sulfuric acid (98%, 17 ml) was gradually dropwise added thereto through the dropping funnel, with vigorously stirring over a period of 30 minutes, in such a way that the reaction temperature did not rise. After addition, the whole was stirred vigorously for further one hour and thereafter it was poured into an ice-water (300 ml), whereupon the white solid as precipitated out was taken out by filtration, washed with water and well dried to obtain bis(2-chloro-4-fluoro-5-nitrophenyl)carbonate (15.7 g, 38.3 mmol) as a white solid product. Yield: 80%. Spectral data of the product are those as shown in Example 4.

EXAMPLE 6:

Bis(2-chloro-4-fluorophenyl)carbonate (45.0 g, 142.6 mmol) was put in a 1000-ml three-neck flask as equipped with a dropping funnel and a stirrer, and sulfuric acid (98%, 250 ml) was added thereto with cooling in an ice-water bath with fully stirring. Next, a mixed acid as prepared from nitric acid (60%, 70 ml) and sulfuric acid (98%, 70 ml) was gradually dropwise added thereto through the dropping funnel, with vigorously stirring over a period of 2 hours, in such a way that the reaction temperature did not rise. After addition, the whole was stirred vigorously for further 2 hours and thereafter it was poured into an ice-water (1000 ml), whereupon the white solid as precipitated out was taken out by filtration, washed with water and dried to obtain bis(2-chloro-4-fluoro-5-nitrophenyl)carbonate (61.9 g) as a white solid product. This was further dried under reduced pressure to give bis(2-chloro-4-fluoro-5-nitrophenyl)carbonate almost quantitatively. Spectral data and other data of the product are those as shown in Example 4.

COMPARATIVE EXAMPLE 1:

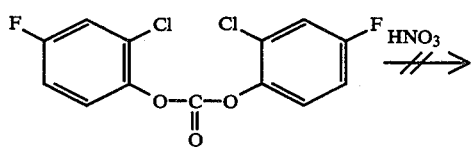

-continued

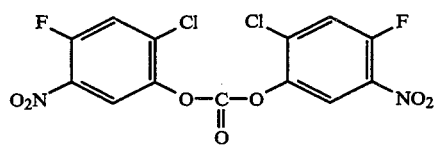

Bis(2-chloro-4-fluorophenyl)carbonate (15.95 g, 50 mmol) was put in a 200-ml three-neck flask as equipped with a dropping funnel and stirrer, and nitric acid (60%, 50 ml) was gradually added thereto with fully stirring and cooling to 0° to 5° C. in an ice-water bath. After dropwise addition, the whole was stirred vigorously for further one hour, and it was poured into an ice-water (500 ml), whereupon the white solid as precipitated out was taken out by filtration, washed with water and then fully dried. The product was identified to be the starting compound of bis(2-chloro-4-fluorophenyl)carbonate from its spectral data.

EXAMPLE 7:

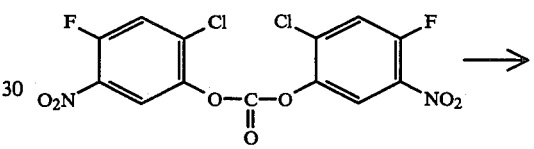

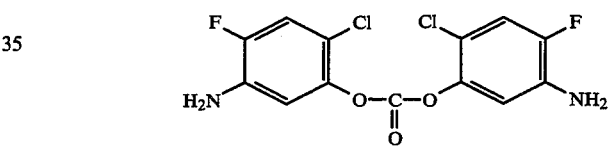

Bis(2-chloro-4-fluoro-5-nitrophenyl)carbonate (233 g, 0.57 mol), toluene (2300 ml) as a solvent, and 5% Pd/C (17.4 g) as a catalyst were put in a 5-liter round-bottom flask as equipped with a stirrer, and hydrogen gas was introduced thereinto with vigorously stirring. With progress of the reaction, the reaction system became exothermic. By introduction of hydrogen gas into the reaction system at such a rate that no hydrogen gas leaked out from the system, the reaction temperature was maintained to fall within the range of from 50° to 60° C. After reaction, the reaction mixture was heated (80° to 100° C.), and the used catalyst was taken out therefrom by filtration. The by-produced water was removed form the resulting filtrate, which was fully dried with anhydrous magnesium sulfate. The drying agent was taken out by filtration, and the solvent was removed by distillation under reduced pressure to obtain bis(2-chloro-4-fluoro-5-aminophenyl)carbonate (143 g, 0.41 mol) as a white solid. Yield: 71.9%.

m.p.: 136.0° to 137.0° C.

$^1$H-NMR(CDCl$_3$): δ 3.83 (4H, brs), 6.71 (2H, d, $J_{HF}$=8.5 Hz), 7.08 (2H, d, $J_{KF}$=10.5 Hz) ppm.

IR (KBr disk): 3500, 1780, 1640, 1510, 1260, 1235, 1190, 1155 cm$^{-1}$.

EXAMPLE 8:

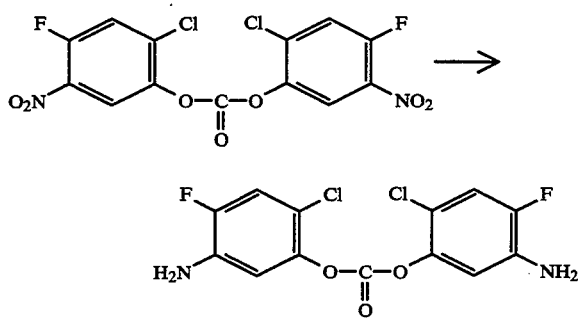

Bis(2-chloro-4-fluoro-5-nitrophenyl)carbonate (1.2 kg, 2.9 mol), toluene (7 liters) as a solvent, and 5% Pd/C (200 g) as a catalyst were put in a 10-liter three-neck flask as equipped with a stirrer, and hydrogen gas was introduced thereinto with vigorously stirring. With progress of the reaction, the reaction system became exothermic. By introduction of hydrogen gas into the reaction system at such a rate that no hydrogen gas leaked out from the system, the reaction temperature was maintained to fall within the range of from 60° to 70° C. After reaction, the reaction mixture was heated (60° to 70° C.), and the used catalyst was taken out therefrom by filtration. The organic layer of the resulting filtrate was separated and was dried with anhydrous magnesium sulfate. The drying agent was taken out by filtration, and the solvent was removed by distillation under reduced pressure to obtain bis(2-chloro-4-fluoro-5-aminophenyl)carbonate (1.01 kg, 2.89 mol) as a white solid. Yield: 99.6%. Melting point, $^1$H NMR spectral data and IR spectral data of the product were same as those in Example 7.

EXAMPLE 9:

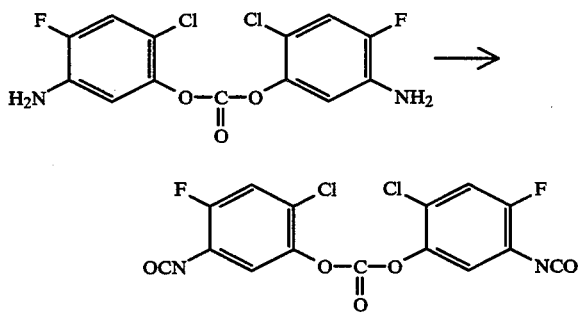

Ethyl acetate (1000 ml) was put in a 3-liter round-bottom three-neck flask as equipped with a stirrer, and phosgene gas as obtained by decomposing trichloromethyl chloroformate (80 ml, 131 g, 0.66 mol) on a heated (50° C.) active charcoal (2.0 g) was introduced thereinto to prepare an ethyl acetate solution of phosgene. To the solution was gradually dropwise added an ethyl acetate (1000 ml) solution of bis(2-chloro-4-fluoro-5-aminophenyl)carbonate (159 g, 0.46 mol). After the the solution was completely added, the whole was heated up to 100° C. so that ethyl acetate was removed by distillation. Ether (300 ml) was added to the crude product thus obtained, and slight amounts of urea derivatives and other formed were removed. Ether was removed by distillation under reduced pressure to obtain bis(2-chloro-4-fluoro-5-isocyanatophenyl)carbonate (185 g, 0.46 mol). Yield: 100%.

m.p.: 108.0° to 109.0° C.

$^1$H-NMR(CDCl$_3$): δ 7.07 (2H, d, $J_{HF}$=8.0 Hz ), 7.29 (2H, d, $J_{HF}$=10.0 Hz) ppm.

IR (KBr disk ): 2250, 1785, 1535, 1465, 1220, 1170 cm$^{-1}$.

EXAMPLE 10:

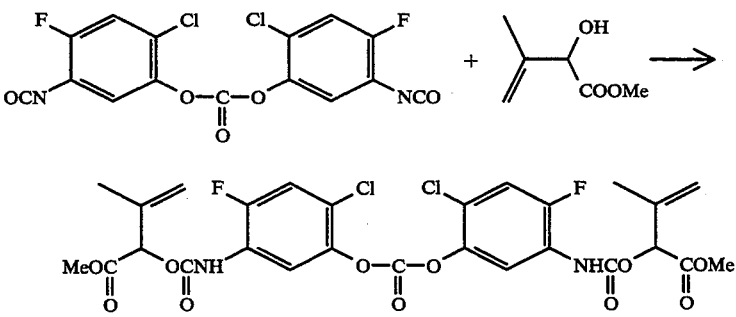

Triethylamine (20 mg, 0.16 mmol) was added to a toluene solution (35 ml) containing bis(2-chloro-4-fluoro-5-isocyanatophenyl)carbonate (1.72 g, 4.29 mmol) and methyl 2-hydroxy-3-methyl-3-butenoate (1.25 g, 9.60 m mmol), and the mixture was stirred for 1.5 hours at room temperature. After reaction, ethyl acetate was added to the reaction liquid, which was then washed with 1N hydrochloric acid and then with water. After drying the organic layer, the solvent was removed therefrom by distillation under reduced pressure to obtain a pale yellow solid of bis [2-chloro-4-fluoro-5-{(1-methoxycarbonyl-2-methyl-2-propenyl)oxycarbonylamino}phenyl]carbonate (2.83 g, 4.28 mmol). Yield: ~100%.

m.p.: 72.0° to 74.0° C.

$^1$H-NMR(CDCl$_3$): δ 1.84 (6H, s), 3.79 (6H, s), 5.13 (2H, br, J=1.5 Hz), 5.22 (2H, s), 5.48 (2H, s), 7.16 (2H, brs), 7.20 (2H, d, $J_{HF}$=10.2 Hz), 8.18 (2H, d, $J_{HF}$=7.6 Hz) ppm.

IR (KBr disk): 1795, 1745, 1540, 1230, 1210 cm$^{-1}$.

EXAMPLE 11:

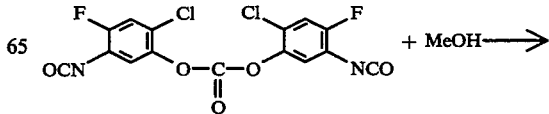

-continued

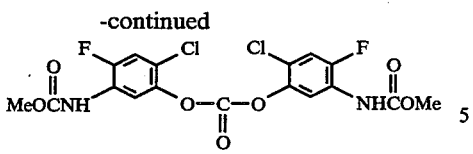

Triethylamine (100 mg, 1.0 mmol) was added to a methanol solution (50 ml) of bis(2-chloro-4-fluoro-5-isocyanatophenyl)carbonate (4.01 g, 10.0 mmol), and the mixture was stirred for 2 hours at room temperature. After reaction, the reaction mixture was poured into 1N hydrochloric acid (100 ml), whereupon bis(2-chloro-4-fluoro-5-methoxycarbonylaminophenyl)carbonate precipitated out as a pale yellow solid (3.95 g, 8.5 mmol). This was isolated by filtration and fully dried. Yield: 85%.

m.p.: 212.0° to 214.0° C.

$^1$H-NMR(CDCl$_3$): δ 3.80 (6H, s), 6.87 (2H, brs), 7.19 (2H, d, $J_{HF}$=10.2 Hz), 8.22 (2H, d, $J_{HF}$=8.3 Hz) ppm.

IR (KBr disk): 1790, 1740, 1630, 1553, 1490, 1420, 1240, 1217 cm$^{-1}$.

EXAMPLE 12:

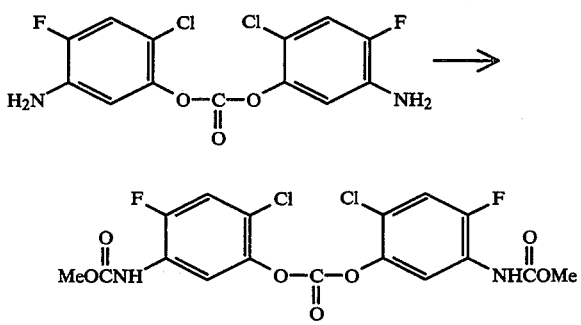

Dry acetone (1500 ml) was added to a mixture comprising bis(2-chloro-4-fluoro-5-aminophenyl)carbonate (233 g, 0.68 mol) and potassium carbonate (188 g, 1.36 mol), and methyl chloroformate (126 g, 1.33 mol) was dropwise added to the resulting solution, and the mixture was heated at 60° C. for 4 hours with stirring. After reaction, acetone was removed by distillation under reduced pressure, acetic acid was added so that the reaction mixture was made acidic, and thereafter the acidic mixture was poured into ice-water. The solid as precipitated out was taken out by filtration, washed with water and fully dried to obtain a white solid of bis(2-chloro-4-fluoro-5-methoxycarbonylaminophenyl)carbonate (279 g, 0.60 mol). Yield: 88.2%. Spectral data and other data of the product are those as shown in Example 11.

EXAMPLE 13:

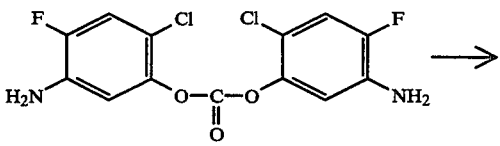

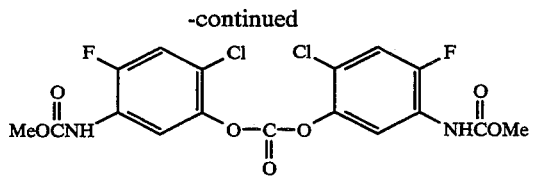

Bis(2-chloro-4-fluoro-5-aminophenyl)carbonate (1.75 kg, 5.0 mol), potassium carbonate (1.04 kg, 7.5 mol), and toluene (6 liters) as a solvent were put in a 10-liter three-neck flask as equipped with a stirrer, a dropping funnel, and a reflux condenser. To the solution was dropwise added methyl chloroformate (770 ml, 9.9 mol), and the whole was stirred at 60° to 70° C. (bath temperature) for 5 hours. After reaction, insoluble desired product deposited was filtrated and washed with toluene, 1N hydrochloric acid and water, and then fully dried to obtain a white solid of bis(2-chloro-4-fluoro-5-methoxycarbonylaminophenyl)carbonate (2.10 kg, 4.51 mol). Yield: 90.2%. Spectral data and other data of the product are those as shown in Example 11.

EXAMPLE 14:

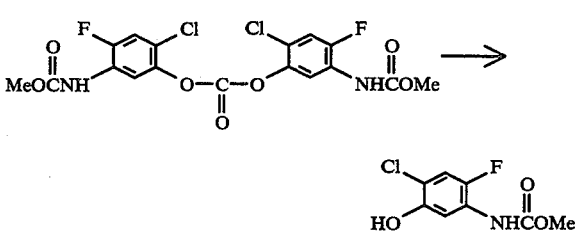

Bis(2-chloro-4-fluoro-5-methoxycarbonylaminophenyl)carbonate (270 g, 0.6 mol), potassium carbonate (83 g, 0.6 mol), and methanol (1.5 liters) as a solvent were put in a 3-liter round-bottom three-neck flask, and the mixture was heated at 50° C. for 2 hours with stirring. After reaction, the reaction mixture was filtered, and the solid product obtained was dissolved in acetic acid (100 ml) and then poured into ice-water with stirring. The white crystals precipitated out were taken out by filtration and fully dried to obtain methyl N-(2-fluoro-4-chloro-5-hydroxyphenyl)carbamate (263 g, 1.20 mol). Yield: 100%.

m.p.: 140.0° to 141.0° C.

$^1$H-NMR(CDCl$_3$): δ 3.79 (3H, s), 5.53 (1H, s), 6.75 (1H, brs), 7.05 (1H, d, $J_{HF}$=10.5 Hz), 7.82 (1H, d, $J_{HF}$=7.5 Hz) ppm.

IR (KBr disk): 1717, 1630, 1560, 1430, 1250 cm$^{-1}$.

EXAMPLE 15:

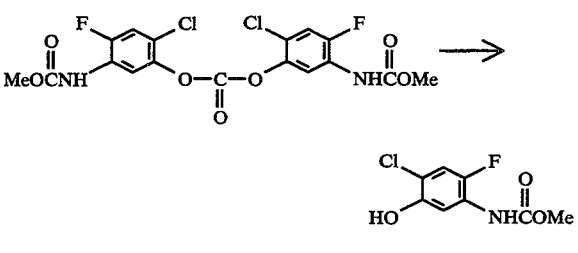

Bis(2-chloro-4-fluoro-5-methoxycarbonylaminophenyl)carbonate (1.28 kg, 2.76 mol), potassium carbonate (286 g, 2.05 mol), and methanol (2.5 liters) as a solvent were put in a 5-liter three-neck flask, and the mixture was heated at 50° C. for 1.5 hours with stirring.

After reaction, the reaction mixture was cooled to room temperature and was poured into 1N hydrochloric acid (10 liter)/ice (5 kg) with stirring. The white solid as precipitated out was taken out by filtration and fully dried to obtain methyl N-(2-fluoro-4-chloro-5-hydroxyphenyl)carbamate (1.20 kg, 5.46 mol). Yield: 99.0%. Spectral data and other data of the product are those as shown in Example 14.

EXAMPLE 16:

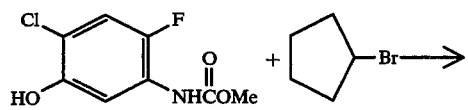

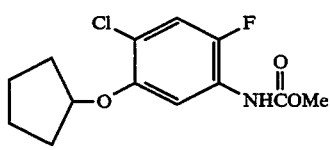

Cyclopentyl bromide (4.07 g, 27.3 mmol) was added to an acetonitrile solution (50 ml) containing methyl N-(2-fluoro-4-chloro-5-hydroxyphenyl)carbamate (5.00 g, 22,8 mmol) and potassium carbonate (1.80 g, 13.0 mmol), and the mixture was heated under reflux for 4 hours. After reaction, the reaction liquid was cooled to room temperature, 1N hydrochloric acid (50 ml) was added thereto, and this was extracted with ethyl acetate (50 ml×2). The organic layer was washed with water and then dried over anhydrous magnesium sulfate. The drying agent was removed by filtration, and the solvent was removed by distillation under reduced pressure to obtain methyl N-(2-fluoro-4-chloro-5-cyclopentyloxyphenyl)carbamate (5.56 g, 19.3 mmol). Yield: 84.8%.

m.p.: 120.0° to 123.0° C.

$^1$H-NMR(CDCl$_3$): δ 2.40–2.10 (8H, m), 3.77 (3H, s), 4.77 (1H, m), 6.82 (1H, brs), 7.07 (1H, d, J$_{HF}$=10.5 Hz), 7.83 (1H, d, J$_{HF}$=7.5 Hz) ppm.

IR (KBr disk): 1714, 1535, 1500, 1415, 1255, 1190 cm$^{-1}$.

EXAMPLE 17:

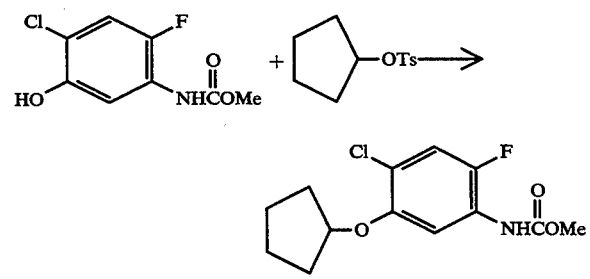

Methyl N-(2-fluoro-4-chloro-5-hydroxyphenyl)carbamate (1.64 kg, 7.47 mol), cyclopentyl p-toluenesulfonate (1.80 kg, 7.48 mol), potassium carbonate (1.03 kg, 7.46 mol) and potassium iodide (12.3 g, 1.0 mol%) were put in a 10-liter three-neck flask as equipped with a stirrer and a reflux condenser, acetone (7.5 liters) as a solvent was added thereto, and the whole was heated under reflux for 4 hours. After reaction, the reaction liquid was taken out, and 0.5N hydrochloric acid (20 liters) was added thereto with vigorously stirring. The white solid of methyl N-(2-fluoro-4-chloro-5-cyclopentyloxyphenyl)carbamate (2.0 kg, 6.95 mol) as precipitated out was isolated by filtration and well dried. Yield: 93.1%. Spectral data and other data of the product are those as shown in Example 16.

EXAMPLE 18:

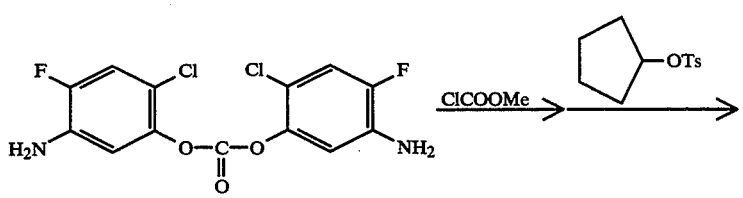

Methyl chloroformate (10.8 g, 0.11 mol) was dropwise added to an acetone solution (100 ml) containing bis(2-chloro-4-fluoro-5-aminophenyl)carbonate (20.0 g, 0.057 mol) and potassium carbonate (23.6 g, 0.71 mol), and the mixture was heated under reflux for 4 hours. Next, the reaction liquid was cooled to room temperature, water (1 ml) was added thereto, and the whole was stirred for 5 hours at a reaction temperature of 40° to 50° C. Subsequently, an acetone solution (40 ml) of cyclopentyl p-toluenesulfonate (26.4 g, 0.11 mol) was added to the reaction liquid and the mixture was heated for 5 hours under reflux. After reaction, acetone was removed by distillation under reduced pressure, acetic acid (200 ml) was added, and the resulting reaction mixture was poured into ice-water (600 ml). The white solid of methyl N-(2-fluoro-4-chloro-5-cyclopentyloxyphenyl)carbamate (13.2 g, 0.048 mol) as precipitated out was isolated by filtration and well dried. Yield: 40%. Spectral data and other data of the product are those as shown in Example 16.

EXAMPLE 19:

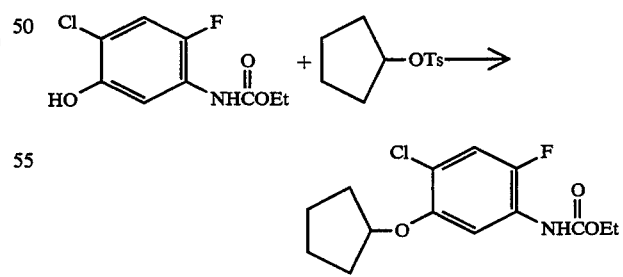

An ethanol solution (20 ml) containing ethyl N-(2-fluoro-4-chloro-5-hydroxyphenyl)carbamate (1.00 g, 4.28 mmol), which was produced in the same manner as in Examples 12 and 13 except that ethyl chloroformate was used in place of methyl chloroformate, and potassium carbonate (0.59 g, 4.28 mmol) was stirred for 2 hours under reflux. Next, cyclopentyl p-toluenesulfonate (1.20 g, 5.14 mmol) was added thereto, and the whole was heated under reflux for further 2 hours. After reaction, the reaction mixture was poured into 1N hydrochloric acid (100 ml). The pale brown solid of ethyl N-(2-fluoro-4-chloro-5-cyclopentyloxyphenyl)-carbamate (1.30 g, 4.28 mmol) as precipitated out was isolated by filtration and fully dried. Yield: ~100%.

m.p.: 92.8° to 97.8° C.

¹H-NMR (CDCl₃): δ 1.33 (3H, t, J=7.0 Hz), 1.40–2.10 (8H, m), 4.32 (2H, q, J=7.0 Hz), 4.88 (1H, m), 6.87 (1H, brs), 7.15 (1H, d, $J_{HF}$=10.5 Hz), 7.92 (1H, d, $J_{HF}$=7.0 Hz) ppm.

IR (KBr disk): 1710, 1535, 1495, 1415, 1255 cm⁻¹.

EXAMPLE 20:

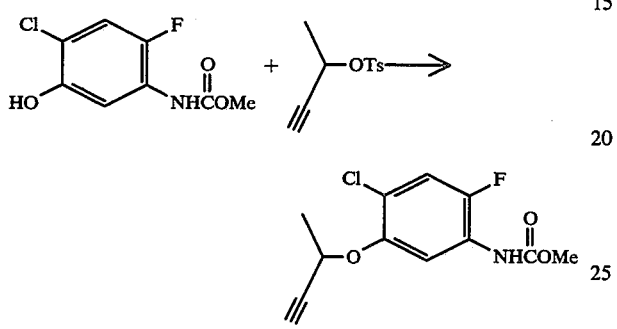

Acetonitrile (600 ml) was added to a mixture comprising methyl N-(2-fluoro-4-chloro-5-hydroxyphenyl)-carbamate (146 g, 0.66 mol), potassium carbonate (91.7 g, 0.66 mol) and 1-butyn-3-yl p-toluenesulfonate (149.1 g, 0.66 mol), and the mixture was heated under reflux for 3 hours. After reaction, the reaction mixture was poured into 1N hydrochloric acid (1500 ml). The pale brown solid of methyl N-{2-fluoro-4-chloro-5-(1-butyn-3-yl)oxyphenyl}carbamate (136 g, 0.50 mol) as precipitated out was isolated by filtration and well dried. Yield: 75.8%.

m.p.: 69.0° to 71.0° C.

¹H-NMR(CDCl₃): δ 1.71 (3H, d, J=6.3 HZ), 2.55 (1H, d, J=1.5 Hz), 3.82 (3H, S), 4.92 (1H, d&q, J=6.3, 1.5 Hz), 7.15 (1H, d, $J_{HF}$=10.0 H₂), 8.09 (1H, d, $J_{HF}$=7.5 Hz) ppm.

EXAMPLE 21:

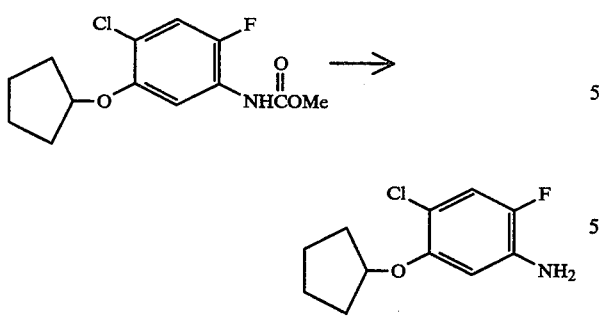

2N sodium hydroxide aqueous solution (3.5 ml) was added to an ethanol solution (1.5 ml) of methyl N-(2-fluoro-4-chloro-5-cyclopentyloxyphenyl)carbamate (1.507 g, 5.24 mmol), and the mixture was heated under reflux for 2 hours. After reaction, the reaction liquid was cooled to room temperature, water was added thereto, and this was extracted with ethyl acetate (20 ml×2). The organic layer was washed with water and saturated brine and then dried over anhydrous magnesium sulfate. The drying agent was taken out by filtration, and the solvent was removed by distillation under reduced pressure, to obtain 2-fluoro-4-chloro-5-cyclopentyloxyaniline (1.20 g, 5.22 mmol). Yield: ~100%.

b.p.: 143° to 145° C./1.5 mmHg.

¹H-NMR(CDCl₃): δ 1.40–2.00 (8H, m), 3.72 (2H, brs), 4.67 (1H, m), 6.39 (1H, d, $J_{HF}$=9.0 Hz), 7.04 (1H, d, $J_{HF}$=11.0 Hz) ppm.

IR (neat): 3500, 3400, 1630, 1510, 1420, 1245, 1185 cm⁻¹.

EXAMPLE 22:

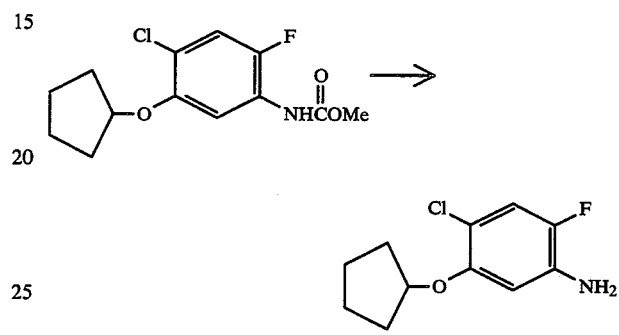

4N potassium hydroxide aqueous solution (4.75 liters) was added to an ethanol solution (3 liters) of methyl N-(2-fluoro-4-chloro-5-cyclopentyloxyphenyl)carbamate (2.25 kg, 7.85 mol) and the mixture was heated under reflux for 5 hours. After reaction, the reaction liquid was cooled to room temperature, water (5 liters) was added thereto, and this was extracted with toluene (5 liters×2). The organic layer was washed with water and then dried over anhydrous magnesium sulfate. The drying agent was taken out by filtration, and the solvent was removed by distillation under reduced pressure to obtain an oily product of 2-fluoro-4-chloro-5-cyclopentyloxyaniline (1.75 kg, 7.62 mol). Yield: 98.3%. Spectral data and other data of the product are those as shown in Example 21.

EXAMPLE 23:

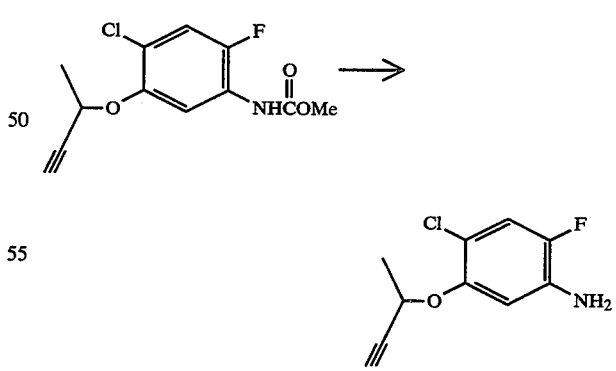

2N sodium hydroxide aqueous solution (660 ml) was added to an ethanol solution (1000 ml) of methyl N-{2-fluoro-4-chloro-5-(1-butyn-3-yl)oxyphenyl}carbamate (326.0 g, 1.2 mol), and the mixture was heated under reflux for 4 hours. After reaction, the reaction liquid was cooled to room temperature and poured into ice-water (2000 ml). The pale brown solid of 2-fluoro-4-chloro-5-(1-butyn-3-yl)oxyaniline (236 g, 1.1 mol) as precipitated out was isolated by filtration and then well dried. Yield: 92.0%.

m.p.: 74.5° to 75.5° C.

$^1$H-NMR(CDCl$_3$): δ 1.60 (3H, d, J=6.3 HZ), 2.48 (1H, d, J=1.5 Hz), 3.46 (2H, brs), 4.72 (1H, d&q, J=6.3, 1.5 Hz), 6.62 (1H, J$_{HF}$=7.5 Hz), 7.01 (1H, d, J$_{Hf}$=10.0 Hz) ppm.

EXAMPLE 24:

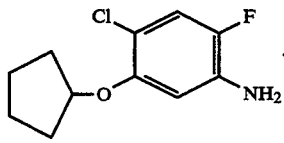

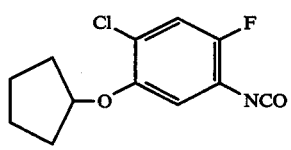

An ethyl acetate solution (5 ml) of trichloromethyl chloroformate (2.00 g, 10.0 mmol) was gradually dropwise added to an ethyl acetate solution (25 ml) of 2-fluoro-4-chloro-5-cyclopentyloxyaniline (2.30 g, 10.0 mmol) at room temperature. After addition, the whole was heated to remove ethyl acetate therefrom by distillation. As a result, 2-fluoro-4-chloro-5-cyclopentyloxyphenylisocyanate was obtained almost quantitatively.

$^1$H-NMR(CDCl$_3$): δ 1.50–2.10 (8H, m), 4.67 (1H, m), 6.60 (1H, d, J$_{HF}$=7.5 Hz), 7.12 (1H, d, J$_{HF}$=10.5 Hz) ppm.

IR (neat): 2275, 1720, 1615, 1525, 1470, 1195 cm$^{-1}$.

EXAMPLE 25:

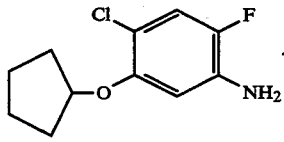

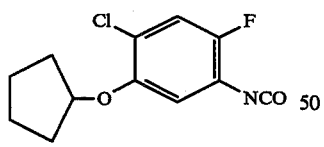

The mixture of trichloromethyl chloroformate (530 ml, 4.4 mol) and toluene (4 liters) were put in a 10-liter three-neck flask as equipped with a stirrer, a dropping funnel, and a reflux condenser, and cooled to 0° C. To the solution was dropwise added a toluene solution (1 liter) containing 2-fluoro-4-chloro-5-cyclopentyloxyaniline (1.0 kg, 2.86 mol) and triethylamine (20 ml) over a period of 8 hours. After addition, the reaction solution was stirred under heat at about 100° C. After reaction, toluene was removed by distillation, and the impurities as precipitated out were removed by filtration. As a result, 2-fluoro-4-chloro-5-cyclopentyloxyphenylisocyanate was obtained almost quantitatively. Spectral data and other data of the product are those as shown in Example 24.

EXAMPLE 26:

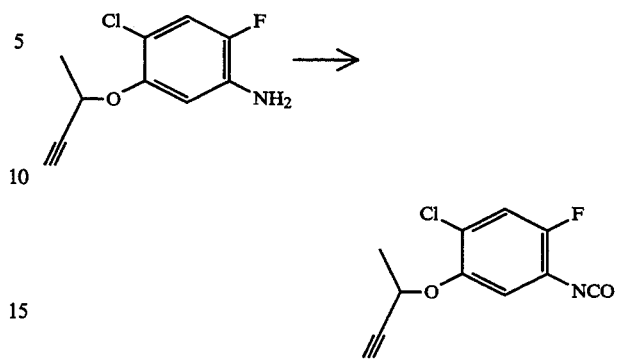

Trichloromethyl chloroformate (283.9 g, 1.44 mol) was gradually dropwise added to an ethyl acetate solution (1500 ml) of 2-fluoro-4-chloro-5-(1-butyn-3-yl)oxyaniline (300 g, 1.4 mol) at room temperature. After addition, the whole was heated to remove ethyl acetate therefrom by distillation, and a brown solid was obtained. To this was added carbon tetrachloride (300 ml). After the insoluble urea derivative formed was taken out by filtration, carbon tetrachloride was removed by distillation under reduced pressure to obtain 2-fluoro-4-chloro-5-(1-butyn-3-yl)oxyphenylisocyanate (315.9 g, 1.32 mol). Yield: 94.3%.

$^1$H-NMR(CDCl$_3$): δ 1.70 (3H, d, J=7.0 Hz), 2.51 (1H, d, J=2.0 Hz), 4.78 (1H, d&q, J=7.0, 2.0 Hz), 6.90 (1H, d, J$_{HF}$=8.0 Hz), 7.19 (1H, d, J$_{HF}$=10.0 Hz) ppm.

IR (KBr disk): 2300, 1615, 1525, 1465, 1195 cm$^{-1}$.

EXAMPLE 27:

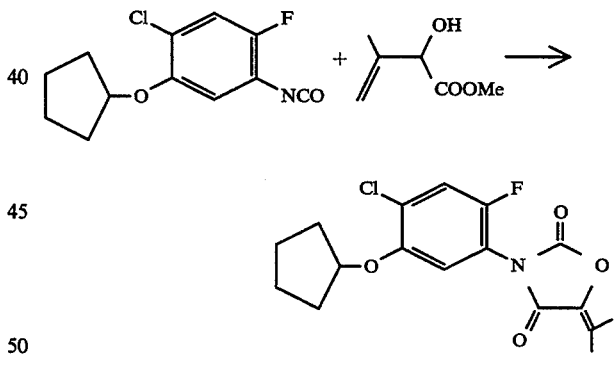

To an ethyl acetate solution (200 ml) containing 2-chloro-4-fluoro-5-cyclopentyloxyphenylisocyanate (203 g, 0.794 mol) and methyl 2-hydroxy-3-methyl-3-butenoate (110 g, 0.794 mol) in a 1-liter three-neck round-bottom flask was added propylene oxide (20 ml, 16.6g, 0.286 mol), and an ethyl acetate solution (30 ml) of triethylamine (8.0 g, 0.0791 mol) was gradually dropwise added thereto with maintaining the temperature of the reaction liquid to be not higher than 50° C. Then, the whole was stirred for 2 hours at the said temperature and thereafter stirred with heating under reflux for 2 hours. After reaction, 1N hydrochloric acid (100 ml) was added to the reaction system, which was then extracted with ethyl acetate (200 ml×2). The organic layer was dried over anhydrous magnesium sulfate, the solvent was removed by distillation therefrom under reduced pressure, and toluene (50 ml) was added thereto. After this was left as it was for a while, a whitish yellow solid of 3N-(2-fluoro-4-chloro-5-cyclopentyloxyphenyl)-5-isopropylidene-1,3-oxazolidine-2,4-dione (201.7 g, 0.57 mmol) precipitated out. Yield: 72%. m.p.: 104.5° to 105.0° C.

$^1$H-NMR(CDCl$_3$): δ 1.58–1.91 (8H, m), 2.00 (3H, s), 2.26 (3H, s), 4.73 (1H, m), 6.77 (1H, d, $J_{HF}$=6.6 Hz), 7.27 (1H, d, $J_{HF}$=8.5 Hz) ppm.

IR (KBr disk): 1820, 1743, 1693 cm$^{-1}$.

EXAMPLE 28:

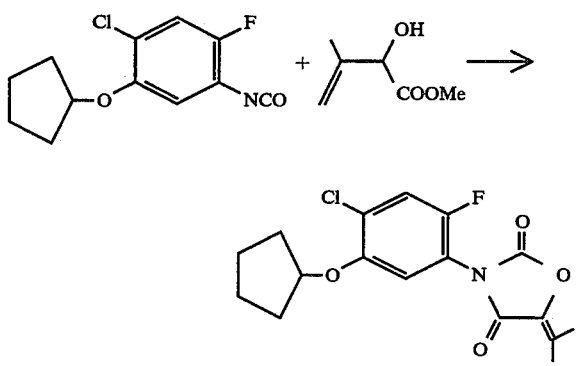

Triethylamine (40 ml) was gradually dropwise added to a toluene solution (10 liters) containing 2-fluoro-4-chloro-5-cyclopentyloxyphenylisocyanate (4.0 kg, 15.6 mol) and methyl 2-hydroxy-3-methyl-3-butenoate (2.4 kg, purity about 90%, 18.4 mol), as put in a 20-liter stainless steel vessel, with cooling in an ice-water bath, in such a way that the temperature of the reaction solution did not rise. The whole was stirred for 2 hours at the determined temperature until the starting materials disappeared by TLC. Next, after addition of potassium carbonate (200 g, 1.45 mol), the reaction mixture was heated in a water bath (100° C.) for 4 hours with stirring with removing the methanol formed therefrom through a distillation device equipped to the reactor. After reaction, the reaction mixture was washed with 1N hydrochloric acid (10 liters) and 1N sodium hydroxide (10 liters) and further with 1N hydrochloric acid (10 liters). The toluene layer was dried over anhydrous magnesium sulfate, the solvent was removed by distillation under reduced pressure, and hexane of about a half of the oily product formed was added to the oily product formed. This was then allowed to stand at room temperature for a while. A whitish yellow solid precipitated out, which was taken out by filtration and well dried to obtain 3N-(2-fluoro-4-chloro-5-cyclopentyloxyphenyl)-5-isopropylidene-1,3-oxazolidine-2,4-dione (4.19 kg, 11.8 mol). Yield: 75.7%. Spectral data and other data of the product are those as shown in Example 27.

EXAMPLE 29:

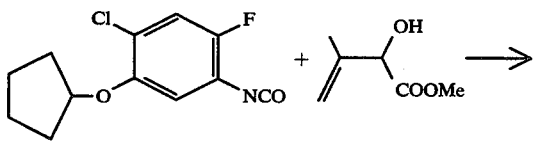

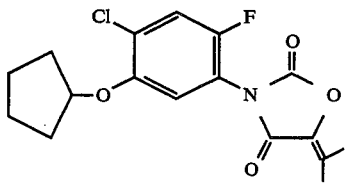

Triethylamine (30 ml) was dropwise added to a toluene solution (5 liter) containing 2-fluoro-4-chloro-5-cyclopentyloxyphenylisocyanate (2.54 kg, 9.93 mol), methyl 2-hydroxy-3-methyl-3-butenoate (1.43 kg, 11.0 mol, purity 94% and propylene oxide (20 ml) in a 10-liter three-neck flask with cooling in an ice-water bath over a period of 40 minutes. After the reactants were reacted (for about 2 hours) until the starting materials disappeared by TLC, they were gradually heated in a water bath (about 100° C.) and were further reacted for about 3 hours at the determined temperature. After reaction, the reaction mixture was cooled to room temperature, and 1N hydrochloric acid (10 liters) was added thereto. The organic layer was separated, and the aqueous layer was extracted with toluene (5 liters×2). The organic layers were combined, washed with 1N hydrochloric acid (10 liters) and water, and dried over anhydrous magnesium sulfate. The drying agent was removed by filtration, toluene was removed by distillation under reduced pressure, hexane of almost the same volume as that of the reddish brown oily product obtained was added, and the whole was allowed to stand at room temperature for a while. A white solid of methyl 2-{N-(2-fluoro-4-chloro-5-cyclopentyloxyphenyl)carbamoyloxy}-3-methyl-3-butenoate (3.96 kg, 10.0 mol) precipitated out, which was taken out by filtration and well dried.

m.p.: 61.5° to 62.5° C.

$^1$H-NMR(CDCl$_3$): δ 1.45–2.05 (11H, m), 3.83 (3H, s), 4.83 (1H, m), 5.17 (1H, brs), 5.26 (1H, s), 5.52 (1H, brs), 7.25 (1H, d, $J_{HF}$=9.0 Hz), 6.91–7.17 (1H, m), 7.87 (1H, d, $J_{HF}$=7.5 Hz) ppm.

IR (KBr disk): 3340, 2980, 1760, 1730, 1545, 1220, 1180 cm$^{-1}$.

Next, a toluene solution (5 liters) containing methyl 2-{N-(2-fluoro-4-chloro-5-cyclopentyloxyphenyl)carbamoyloxy}-3-methyl-3-butenoate (1.6 kg, 4.15 mol) prepared above and potassium carbonate (20 g) was put in a 10-liter three-neck flask and stirred for about 10 hours in a water bath of about 100° C. After reaction, the reaction liquid was cooled to room temperature, 1N hydrochloric acid (10 liters) was added thereto, and the organic layer was separated. The aqueous layer was extracted with toluene (5 liters×2). The organic layers were combined, washed with water, and dried over anhydrous magnesium sulfate. The drying agent was removed by filtration, toluene was removed by distillation under reduced pressure, hexane of almost the same volume as that of the brown oily product obtained was added, and the whole was allowed to stand at room temperature for a while. A white solid of 3N-(2-fluoro-4-chloro-5-cyclopentyloxyphenyl)-5-isopropylidene-1,3-oxazolidine-2,4-dione (1.47 kg, 4.15 mol) precipitated out, which was taken out by filtration and well dried. Yield: 100%. Spectral data and other data of the product are those shown in Example 27.

EXAMPLE 30:

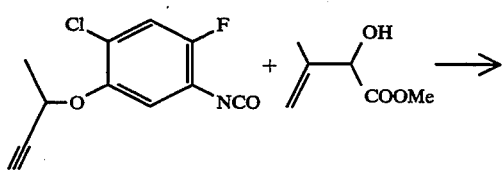

An ethyl acetate solution (10 ml) of triethylamine (1.02 g, 0.01 mol) was gradually dropwise added to an ethyl acetate solution (100 ml) containing 2-chloro-4-fluoro-5-(1-butyn-3-yl)oxyphenylisocyanate (24.0 g, 0.1 mol), methyl 2-hydroxy-3-methyl-3-butenoate (14.3 g, 0.11 mol), and propylene oxide (1 ml) in such a way that the liquid temperature did not rise over 50° C., and the whole was then stirred for further 2 hours with heating under reflux. After reaction, 1N hydrochloric acid (50 ml) was added to the reaction liquid, which was then extracted with ethyl acetate (100 ml×2). The organic layer was dried with anhydrous magnesium sulfate, the solvent was removed by distillation under reduced pressure, and the crude product formed was recrystallized from toluene/hexane to obtain a whitish yellow solid of 3N-{2-fluoro-4-chloro-5-(1-butyn-3-yl)oxyphenyl}-5-isopropylidene-1,3-oxazolidine-2,4-dione (28.71 g, 0.085 mol). Yield: 85%.

m.p.: 102.0° to 103.0° C.

$^1$H-NMR (CDCl$_3$): δ 1.70 (3H, d, J=6.0 Hz), 2.03 (3H, s), 2.28 (3H, s), 2.52 (1H, d, J=1.5 Hz), 4.80 (1H, d&q, J=6.0 Hz, 1.5 Hz), 7.12 (1H, d, J$_{HF}$=6.0 Hz), 7.32 (1H, d, J$_{HF}$=9.0 Hz) ppm.

IR (KBr disk): 2120, 1820, 1736, 1680, 1505, 1430, 1375, 1200 cm$^{-1}$.

EXAMPLE 31:

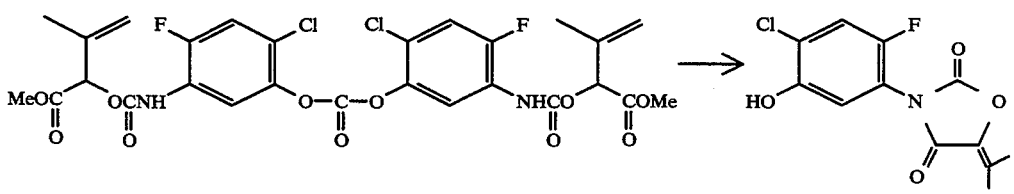

Acetic acid (10 ml) was added to a mixture comprising bis[2-chloro-4-fluoro-5{(1-methoxycarbonyl-2-methyl-2-propenyl)oxycarbonylamino}phenyl]carbonate (1.36 g, 2.1 mmol) and potassium carbonate (0.50 g, 3.62 mmol) and heated for 2 hours with stirring. After reaction, the reaction mixture was cooled and then poured into ice-water. The solid as precipitated out was taken out by filtration and well dried to obtain a white solid of 3N-(2-fluoro-4-chloro-5-hydroxyphenyl)-5-isopropylidene-1,3-oxazolidine-2,4-dione (0.97 g, 3.40 mmol). Yield: 82.6%.

$^1$H-NMR(CDCl$_3$): δ 2.06 (3H, s), 2.29 (3H, s), 5.78 (1H, brs), 6.98 (1H, d, J$_{HF}$=7.0 Hz), 7.25 (1H, d, J$_{HF}$=4.5 Hz) ppm.

IR (KBr disk): 1820, 1738, 1685, 1505, 1395, 1305, 1200 cm$^{-1}$.

EXAMPLE 32:

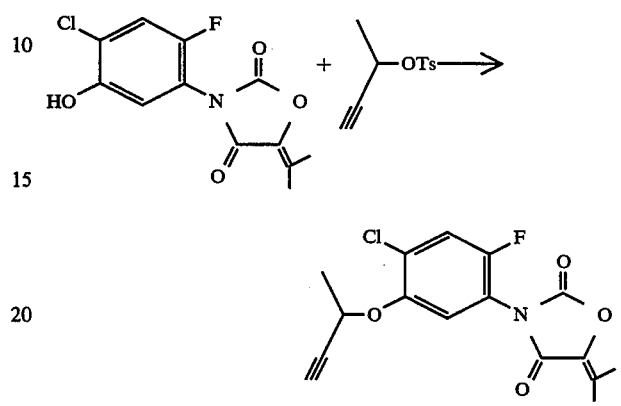

Acetonitrile (50 ml) was added to a mixture comprising 3N-(2-fluoro-4-chloro-5-hydroxyphenyl)-5-isopropylidene-1,3-oxazolidine-2,4-dione (5.0 g, 15.7 mmol), 1-butyn-3-yl p-toluenesulfonate (4.0 g, 17.8 mmol) and potassium carbonate (1.5 g, 10.9 mmol), and the reaction mixture was heated for 4 hours under reflux. After reaction, acetonitrile was removed by distillation under reduced pressure, and 1N hydrochloric acid (100 ml) was added to the residue, which was then extracted with ether (50 ml×2). After dried, ether was removed by distillation under reduced pressure, and an oily product of 3N-{2-fluoro-4-chloro-5-(1-butyn-3-yl)oxyphenyl}-5-isopropylidene-1,3-oxazolidine-2,4-dione was obtained. This was recrystallized from ether/hexane, and a pure product (4.94 g, 14.6 mmol) was obtained. Yield: 83.6%. Spectral and other data of the product are those as shown in Example 30.

EXAMPLE 33:

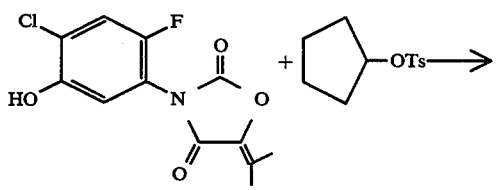

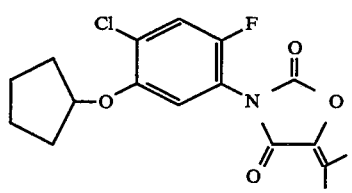

An acetonitrile solution (100 ml) containing 3N-(2-fluoro-4-chloro-5-hydroxyphenyl)-1,3-oxazolidine-2,4-dione (1.0 g, 3.50 mmol), cyclopentyl p-toluenesulfonate (1.0 g, 4.16 mmol) and potassium carbonate (0.5 g, 3.62 mmol) was heated for 4 hours under reflux. After reaction, the mixture was poured into water (100 ml) and extracted with ethyl acetate (50 ml×3). The organic layer was washed with saturated sodium hydrogencarbonate aqueous solution (50 ml) and saturated brine (50 ml) and then dried over anhydrous magnesium sulfate. The drying agent was removed by filtration, the solvent was removed by distillation, and 3N-(2-fluoro-4-chloro-5-cyclopentyloxyphenyl)-5-isopropylidene-1,3-oxazolidine-2,4-dione was obtained. This was purified by silica gel chromatography (ethyl acetate/hexane=$\frac{1}{2}$) to obtain a white solid of the intended product (0.99 g, 2.80 mmol). Yield: 80.0%. Spectral and other data of the product are those as shown in Example 27.

While the invention has been described in detail and with reference to specific embodiments thereof, it will be apparent to one skilled in the art that various changes and modifications can be made therein without departing from the spirit and scope thereof.

What is claimed is:

1. A compound of the formula (11)

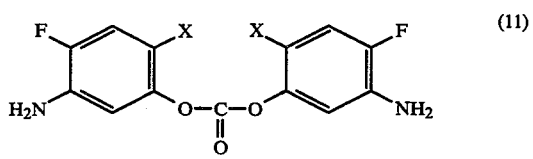

where X represents a halogen atom.

2. A compound as claimed in claim 1, in which X is a chlorine atom.

* * * * *